US00PP09168P

United States Patent [19]

Hofmann

[11] Patent Number: Plant 9,168

[45] Date of Patent: Jun. 13, 1995

[54] VARIETY OF GERANIUM NAMED 'FIRST KISS'

[75] Inventor: Christa Hofmann, Grossdittmannsdorf, Germany

[73] Assignee: Oglevee, Ltd., Connellsville, Pa.

[21] Appl. No.: 334,854

[22] Filed: Nov. 1, 1994

[51] Int. Cl.[6] ..... A01H 5/00
[52] U.S. Cl. ..... Plt./87.12
[58] Field of Search ..... Plt. 87.12

*Primary Examiner*—James R. Feyrer
*Attorney, Agent, or Firm*—Webb Ziesenheim Bruening Logsdon Orkin & Hanson

[57] ABSTRACT

The new cultivar is generally characterized by a bright and bold two tone pink bi-color which is outstanding above a compact, medium green foliage. This variety will work well for both the grower and the home gardener with its ease of rooting, the controlled habit, free branching and flowering.

1 Drawing Sheet

BACKGROUND OF THE INVENTION

The present invention comprises a new and distinct cultivar of *Pelargonium*×*hortorum* known by the varietal name 'First Kiss' (Oglevee No. 2166, Breeder No. P-575). The new variety was discovered in a selected breeding program in Dresden, Germany in May of 1991. The new variety is a selection from the cross-breeding of several breeding-lines which are unnamed, but which are maintained proprietary for breeding purposes. The new variety was first asexually reproduced by cuttings at Dresden, Germany on Aug. 2, 1991. The new variety has been asexually reproduced by cuttings at Oglevee, Ltd. in Connellsville, Pa. over a two year period starting Apr. 1, 1992. It has also been trial and field tested at Connellsville and has been found to retain its distinctive characteristics through successive propagations.

The cultivar, when grown in a glass greenhouse in Connellsville, Pa. using natural light and 60° F. night and 72° F. day, has a response time of six weeks from a rooted cutting to flowering in a 10 cm. pot. The response time was determined on plants grown in soilless media employing constant fertilizer 200 parts per million of nitrogen and potassium in full light. The rooted cuttings were potted on Feb. 23, 1994 and flowered on Apr. 7, 1994.

DESCRIPTION OF THE DRAWING

FIG. 1 of the accompanying photographic drawing illustrates the new cultivar the color being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee, Ltd. in Connellsville, Pa. The plant history was taken on six week plants in a 15 cm pot blossomed under natural light in a greenhouse and the color readings were taken indoors under 200–220 foot candles of fluorescent cool white light. Color references are primarily to the R.H.S. Colour Chart of The Royal Horticultural Society of London.

THE PLANT

Classification:

*Botanical.*—*Pelargonium*×*hortorum.*
*Commercial.*—Zonal florists' geranium.

Form: Compact mound form.
- *Height.*—15.0–17.0 cm from media surface.
- *Growth.*—Compact, semi-dwarf; free branching; free flowering with semi-double flowers.

Strength: Stands upright without artificial support.

Foliage: Stalked leaf attachment.

Leaves:
- *Size.*—7.5–8.5 cm across; fully expanded leaf.
- *Shape.*—Reniform, Cordate base.
- *Margin.*—Crenate.
- *Texture.*—Slightly pubescent; leathery.
- *Color.*—Top: Green Group 137B. Bottom: Green Group 137D.
- *Zone.*—No zone present.
- *Ribs and veins.*—Venation: Palmate. Color: Green Group 138B.

Petioles:
- *Color.*—Yellow-Green Group 146A.
- *Length.*—4.0–6.5 cm.

Stem:
- *Color.*—Yellow-Green Group 146A.
- *Internodes.*—1.5–4.0 cm in length.

THE BUD

Shape: Upright hemispherical cluster.

Size: 2.0–3.5 cm across.

INFLORESCENCE

Blooming habit: Free and early flowering; semi-double; slow to shatter.

Size: Closed: 1.0–1.5 cm; and bud showing faintest hint of color. Fully Open: 9.0–12.0 cm.

Borne: Umbel; florets on pedicel; pedicel on peduncle; 13.0–16.0 cm above the foliage.

Open florets:
- *Form.*—Semi-double; flat to slightly cupped.
- *Color.*—Top: Upper two petals: Base: Red Group 56C. Middle: Red Group 55A. Veining: Red Group 54A. Edge: Red Group 56C. Lower petals: Base: Red Group 56C. Middle: Red-Purple Group 57B Edge: Red Group 56C. Bottom: Overall color Red Group 56C with a slight veining to Red Group 55C.
- *Petals.*—Single, not united; margin entire; obovate; flat to slightly cupped; 6–9 in number.

*Size.*—4.0–5.0 cm across.

Closed florets:

*Bud size.*—1.0–1.5 cm.

*Color.*—Shows only faintest hint of color.

Texture and appearance: Smooth, slightly reflective; Appearance from a distance is a very distinct light pink/dark pink bi-color flower above medium green foliage.

Petaloids:

*Quantity.*—0–2.

*Shape.*—Flat, twisted.

*Color.*—Top: Red Group 56D. Bottom: Red Group 56D.

Pedicel:

*Length.*—2.5–3.5 cm.

*Color.*—Yellow-Green Group 146C.

Peduncle: 12.0–17.0 cm in length.

*Color.*—Yellow-Green Group 146B.

Disease resistance: Not known.

REPRODUCTIVE ORGANS

Stamens:

*Anthers.*—1.0–2.0 mm in length.

*Filaments.*—5.0–7.0 mm in length.

*Pollen.*—Golden Brown.

Pistils:

*Number.*—1.

*Length.*—8.0–9.0 mm.

*Stigma.*—5–6 parted, Red purple.

*Style.*—2.0–2.5 mm in length; Red purple.

Ovaries: Superior; pubescent; pale green; 3.0–4.0 mm in length.

Fruit: None observed.

GENERAL CHARACTERISTICS

'First Kiss' provides a bright and bold two tone pink bi-color which is outstanding above a compact, medium green foliage. This variety will work well for both the grower and the home gardener with its ease of rooting, the controlled habit, free branching and flowering.

I claim:

1. A new and distinct variety of geranium plant substantially as shown and described.

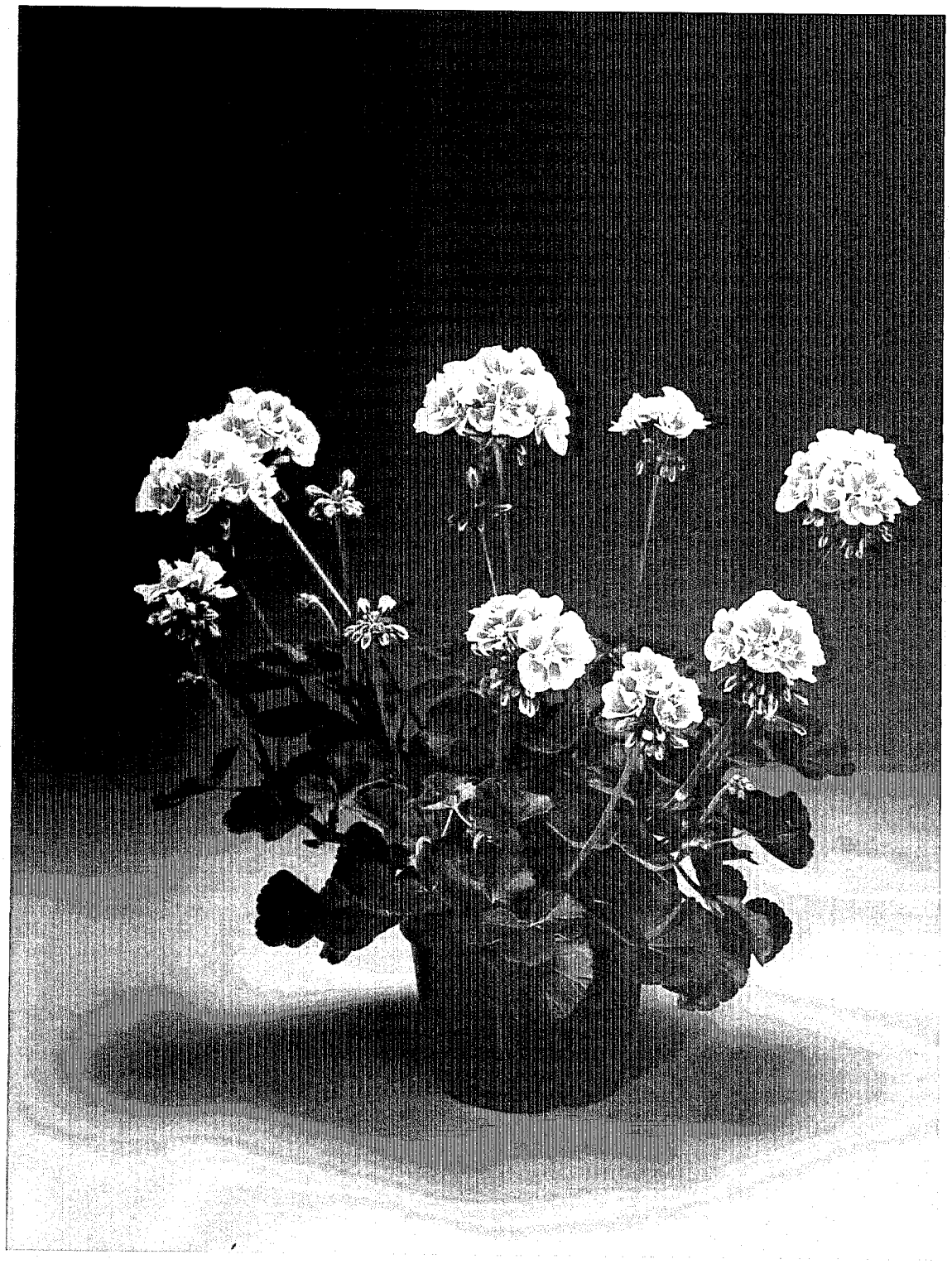

* * * * *